| United States Patent [19] | [11] 4,052,476 |
|---|---|
| Morrison | [45] Oct. 4, 1977 |

[54] TOLUENE DISPROPORTIONATION OVER ZEOLITE CATALYST

[75] Inventor: Roger A. Morrison, West Deptford, N.J.

[73] Assignee: Mobil Oil Corporation, New York, N.Y.

[21] Appl. No.: 657,411

[22] Filed: Feb. 12, 1976

Related U.S. Application Data

[63] Continuation-in-part of Ser. No. 571,122, April 24, 1975, abandoned, which is a continuation-in-part of Ser. No. 431,519, Jan. 7, 1974, abandoned.

[51] Int. Cl.$^2$ .............................................. C07C 3/62
[52] U.S. Cl. .............................................. 260/672 T
[58] Field of Search .................................. 260/672 T

[56] References Cited

U.S. PATENT DOCUMENTS

| 3,751,504 | 8/1973 | Keown et al. ....................... 260/671 |
| 3,790,471 | 2/1974 | Arqzurer et al. ................. 260/672 T |
| 3,855,328 | 12/1974 | Hedge ............................... 260/672 T |

*Primary Examiner*—C. Davis
*Attorney, Agent, or Firm*—Charles A. Huggett; Raymond W. Barclay; Dennis P. Santini

[57] ABSTRACT

A process is provided for disproportionation of toluene in a reaction zone maintained under conditions such that said disproportionation is accomplished in the vapor-phase, with a hydrogen/hydrocarbon mole ratio of from 0 to 4, and in the presence of a catalyst comprising a crystalline aluminosilicate zeolite characterized by a silica/alumina mole ratio of at least 12 and a constraint index, hereinafter defined, within the approximate range of 1 to 12, said catalyst under said conditions being capable of long stability and of affording a high yield of disproportionation products with favorable selectivity toward para-xylene.

23 Claims, No Drawings

TOLUENE DISPROPORTIONATION OVER ZEOLITE CATALYST

CROSS-REFERENCE TO RELATED APPLICATIONS

This is a continuation-in-part of application Ser. No. 571,122, filed Apr. 24, 1975 now abandoned, which was a continuation-in-part of application Ser. No. 431,519, filed Jan. 7, 1974, now abandoned.

BACKGROUND OF THE INVENTION

1. Field of the Invention

This invention is directed to the vapor-phase disproportionation of toluene with a very low hydrogen to hydrocarbon mole ratio and in the presence of a crystalline aluminosilicate zeolite characterized by a silica/alumina mole ratio of at least 12, a constraint index within the approximate range of 1 to 12 and exceptionally long catalyst life, being capable of affording high yield of disproportionation product, a favorable selectivity toward para-xylene, and which is easily and effectively regenerated, when necessary, without substantial loss in activity.

2. Discussion of the Prior Art

U.S. Pat. No. 3,551,509 discloses transalkylation between trimethylbenzenes and toluene to yield xylenes and benzene in the presence of a crystalline aluminosilicate catalyst having pore openings of 8 to 15 Angstrom units and, preferably containing Group VIII metals, hydrogen and rare earth cations. The above patent is also the subject of U.S. Pat. No. Re. 27,639. From the teaching of these patents, one would expect that the rather large pore openings of 8 to 15 Angstrom units is a requirement for effective transalkylation of polyalkylaromatic hydrocarbons with aromatic hydrocarbons such as toluene.

In the area of aromatic disproportionation, Grandio et al. teach in the *Oil and Gas Journal*, Vol. 69, Number 48(1971) a liquid-phase toluene disproportionation process utilizing zeolite catalysts in the absence of hydrogen. They further teach that vapor-phase toluene disproportionation requires hydrogen recycle or else frequent regeneration of catalyst to keep coke levels low on the catalyst and to maintain catalytic activity over any reasonable period of time.

Otani teaches in *Chemical Engineering*, 77(16), 118(1970) that vapor-phase catalytic disproportionation of toluene requires hydrogen recycle to keep the zeolite catalyst from excessive coke build-up and, thereby, maintain reasonable catalyst activity.

U.S. Pat. Nos. 3,126,422; 3,413,374; 3,598,878; 3,598,879; and 3,607,961 show vapor-phase disproportionation of toluene over various catalysts.

Unfortunately, while the crystalline aluminosilicate catalysts proposed for such prior art methods provide satisfactory initial yields of desired products of disproportionation, for the most part, their catalytic aging properties are not sufficiently good enough to warrant commercial application, even with high hydrogen to hydrocarbon ratios. Hence, it is of advantage to provide a satisfactory process for toluene disproportionation using a crystalline aluminosilicate zeolite catalyst which has improved aging properties, i.e. maintains disproportionation in high yield over a long, commercially attractive period of time, heretofore lacking in the art. Added advantage for the present process is that very little or no hydrogen is required and that the para-xylene content of the xylenes produced is higher than equilibrium predictions.

SUMMARY OF THE INVENTION

This invention contemplates a process for effecting vapor-phase toluene disproportionation which comprises contacting a toluene charge under conditions effective for accomplishing said vapor-phase disproportionation, including a reactor inlet temperature between about 650° F and about 1100° F, a pressure between atmospheric and 1000 psig, a total feed weight hourly space velocity (WHSV) between about 1 and about 20 and a low hydrogen to hydrocarbon mole ratio of 0 to about 4 with a catalyst composition comprising a crystalline aluminosilicate zeolite characterized by a silica/alumina mole ratio of greater than 12 and a constraint index of from about 1 to about 12. The above WHSV is based upon the weight of catalyst composition, i.e. total weight of active catalyst and binder therefor.

The crystalline aluminosilicate zeolites used in the catalyst composition of the process of this invention are referred to generally as ZSM-5 type or as behaving like ZSM-5 and are represented by the general formulas, expressed in terms of mole ratios of oxides in the anhydrous state, as follows:

ZSM-5
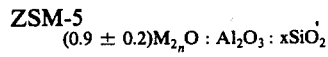

wherein M is a cation, predominantly non-noble metal of Group VIII of the Periodic Table and/or hydrogen, $n$ is the valence of M and $x$ is at least 5, ZSM-11
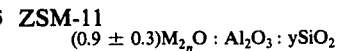

wherein M is a cation, predominantly non-noble metal of Group VIII of the Periodic Table and/or hydrogen, $n$ is the valence of M and $y$ is from 20 to 90, ZSM-12
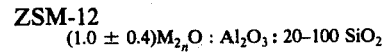

wherein M is a cation, predominantly non-noble metal of Group VIII of the Periodic Table and/or hydrogen and $n$ is the valence of M, ZSM-35 and ZSM-38
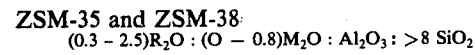

wherein R is an organic nitrogen-containing cation derived from ethylenediamine or pyrrolidine for ZSM-35 and from a 2-(hydroxyalkyl) trialkylammonium compound, wherein alkyl is methyl, ethyl or a combination thereof, for ZSM-38, and M is a cation, predominantly non-noble metal of Group VIII of the Periodic Table and/or hydrogen.

DESCRIPTION OF SPECIFIC EMBODIMENTS

The catalyst composition useful in this invention comprises a crystalline aluminosilicate zeolite characterized by a silica/alumina mole ratio of at least 12 and a constraint index of from about 1 to about 12, non-limiting examples of which include ZSM-5, ZSM-11, ZSM-12, ZSM-35 and ZSM-38.

Zeolite ZSM-5 is taught by U.S. Pat. No. 3,702,886, issued Nov. 14, 1972, the disclosure of which is incorporated herein by reference. In a preferred synthesized form, the zeolite ZSM-5 for use in the catalyst composition useful in this invention has a formula, in terms of mole ratios of oxides in anhydrous state, as follows:

$$(0.9 \pm 0.2)M_{2/n}O : Al_2O_3 : xSiO_2$$

wherein M is selected from the group consisting of a mixture of alkali metal cations, especially sodium, and tetraalkylammonium cations, the alkyl groups of which preferably contain 2 to 5 carbon atoms, and x is at least 5. Particularly preferred is a zeolite having the formula in the anhydrous state as follows:

$$(0.9 \pm 0.2)M_{2/n}O : Al_2O_3 : ZSiO_2$$

wherein Z is from greater than 30 to about 350 or higher.

Zeolite ZSM-11 is taught by U.S. Pat. No. 3,709,979, issued Jan. 9, 1973, the disclosure of which is incorporated herein by reference. In the as synthesized form, the zeolite ZSM-11 for use in the catalyst composition useful in this invention has a formula, in terms of mole ratios of oxides in the anhydrous state, as follows:

$$(0.9 \pm 0.3)M_{2/n}O : Al_2O_3 : 20 \text{ to } 90 \text{ SiO}_2$$

wherein M is a mixture of at least one of the quaternary cations of a Group V-A element of the Periodic Table and alkali metal cations, especially sodium. The original cations can be present so that the amount of quaternary metal cations is between 10 and 90 percent of the total amount of the original cations. Thus, the zeolite can be expressed by the following formula in terms of mole ratios of oxides:

$$(0.9 \pm 0.3)(xXR_4+1-xM_{2/n}O) : Al_2O_3 : 20 \text{ to } 90 \text{ SiO}_2$$

wherein R is an alkyl or aryl group having between 1 and 7 carbon atoms, M is an alkali metal cation, X is a group V-A element, especially a metal, and x is between 0.1 and 0.9.

Zeolite ZSM-12 is taught by U.S. Pat. No. 3,832,449, issued Aug. 27, 1974, the disclosure of which is incorporated herein by reference.

ZSM-35 is described in U.S. application Ser. No. 528,061, filed Nov. 29, 1974. This zeolite can be identified, in terms of mole ratios of oxides and in the anhydrous state, as follows:

$$(0.3 - 2.5)R_2O : (O - 0.8)M_2O : Al_2O_3 : > 8 \text{ SiO}_2$$

wherein R is an organic nitrogen-containing cation derived from ethylenediamine or pyrrolidone and M is an alkali metal cation, and is characterized by a specified X-ray powder diffraction pattern.

In a preferred synthesized form, zeolite ZSM-35 has a formula, in terms of mole ratios of oxides and in the anhydrous state, as follows:

$$(0.4 - 2.5)R_2O : (O - 0.6)M_2O : Al_2O_3 : xSiO_2$$

wherein R is an organic nitrogen-containing cation derived from ethylenediamine or pyrrolidone, M is an alkali metal, especially sodium, and x is from greater than 8 to about 50.

ZSM-38 is described in U.S. application Ser. No. 560,412, filed Mar. 20, 1975. This zeolite can be identified, in terms of mole ratios of oxides and in the anhydrous state, as follows:

$$(0.3 - 2.5)R_2O : (O - 0.8)M_2O : Al_2O_3 : > 8 \text{ SiO}_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4 - 2.5)R_2O : (O - 0.6)M_2O : Al_2O_3 : xSiO_2$$

wherein R is an organic nitrogen-containing cation derived from a 2-(hydroxyalkyl) trialkylammonium compound, wherein alkyl is methyl, ethyl or a combination thereof, M is an alkali metal, especially sodium, and x is from greater than 8 to about 50.

The original cations of the above zeolites ZSM-5, ZSM-11, ZSM-12, ZSM-35 and ZSM-38 are replaced, in accordance with techniques well known in the art, at least in part, by ion exchange with hydrogen or hydrogen precursor cations and/or non-noble metal ions of Group VIII of the Periodic Table, i.e. nickel, iron and/or cobalt.

Although the zeolites herein described have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of the zeolites for use herein is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratio of at least about 30.

Such catalysts, after activation, acquire an intracrystalline sorption capacity for normal hexane which is greater than that for water, i.e. they exhibit "hydrophobic" properties. It is believed that this hydrophobic character is advantageous in the present invention.

The present invention provides a highly effective disproportionation process with a catalyst, the crystalline aluminosilicate zeolite portion of which, as suggested above, has a smaller pore size than those crystalline aluminosilicates previously used for such purpose. An example of this is zeolite ZSM-5 which has elliptical pores of approximately 4.8 × 7.1 Angstrom units.

The type zeolites useful in this invention freely sorb normal hexane and have a pore dimension greater than about 5 Angstroms, or, if elliptical in pore shape, at least the size of the pores in ZSM-5. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. Also, structures can be conceived due to pore blockage or other cause, that may be operative.

Rather than attempt to judge from crystal structure whether or not a catalyst possesses the necesssary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts, including those useful herein, are:

| Crystalline Aluminosilicate | CI |
|---|---|
| ZSM-5 | 8.3 |
| ZSM-11 | 8.7 |
| ZSM-12 | 2 |
| ZSM-35 | 2 |
| ZSM-38 | 2 |
| Beta | 0.6 |
| ZSM-4 | 0.5 |
| H-Zeolon | 0.5 |
| REY | 0.4 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F to 950° F, with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F to 950° F, the constraint index will have a value for any given zeolite of interest herein within the approximate range of 1 to 12.

The specific zeolites described, when prepared in the presence of organic cations, are catalytically inactive, possibly because the intracrystalline free space is occupied by organic cations from the forming solution. They may be activated by heating, for example, in an inert atmosphere at 1000° F for one hour, followed by base exchange with ammonium salts and by calcination at 1000° F in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and cliniptilolite. The preferred crystalline aluminosilicate are ZSM-5, ZSM-11, ZSM-12, ZSM-35 and ZSM-38, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired for the present process. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

Members of the above zeolites useful herein have an exceptionally high degree of thermal stability thereby rendering them particularly effective for use in processes involving elevated temperatures. In this connection, this group of zeolites appear to be some of the most stable zeolites known to date. However, it has been found that the process of this invention may be carried out at reactor bed temperatures not in excess of about 1100° F, which eliminates many undesirable reactions that occur in catalytic disproportionation of hydrocarbons carried out at higher temperatures. The deleterious effects of these reactions cause several basic problems for disproportionation processes. At reactor bed temperatures substantially above 1100° F, the reactants and the products undergo degradation resulting in the loss of desired products and reactants. Undesirable residues are formed from the degradation reactions. These degradation products may lead to the formation of coke-like deposits on the active surfaces of the catalyst. As a result, these deposits rapidly destroy the high activity of the catalyst and greatly shorten its effective life. Such undesirable effects are obviated under the conditions and with the catalyst employed in the present process.

Members of the above group of zeolites for use in the catalyst composition of the present invention possess definite distinguishing crystalline structures as evidenced by the above U.S. patents incorporated herein by reference.

The synthetic ZSM-35 zeolite possesses a definite distinguishing crystalline structure whose X-ray diffraction pattern shows substantially the significant lines set forth in Table 1.

TABLE 1

| Interplanar Spacing | Relative Intensity |
|---|---|
| 9.6 ± 0.20 | Very Strong-Very, Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium-Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak-Medium |
| 3.14 ± 0.06 | Weak-Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

The synthetic ZSM-38 zeolite possesses a definite distinguishing crystalline structure whose X-ray diffraction patterns shows substantially the significant lines set forth in Table 1A.

TABLE 1A

| Interplanar Spacing | Relative Intensity |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

These values were determined by standard technique. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart From these, the relative intensities, 100 $I/I_o$, where $I_o$ is the intensity of the strongest line or peak, and k (obs.), the interplanar spacing in the Angstrom units, corresponding to the recorded lines, were calculated. It should be understood that these X-ray diffraction patterns are characteristic of all the species of the above respectively identified zeolites. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

Zeolites ZSM-5, ZSM-11 and ZSM-12 for use in the process of this invention are prepared as indicated in their respective patents, incorporated herein by reference above.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

TABLE 2

|  | Broad | Preferred |
|---|---|---|
| $R^+$ | 0.2 – 1.0 | 0.3 – 0.9 |
| $\dfrac{R^+ + M^+}{OH^-/SiO_2}$ | 0.05 – 0.5 | 0.07 – 0.49 |
| $H_2O/OH^-$ | 41 – 500 | 100 – 250 |
| $SiO_2/Al_2O_3$ | 8.8 – 200 | 12 – 60 | wherein R is an organic nitrogen-containing cation derived from pyrrolidone or ethylenediamine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° F to about 400° F for a period of time of from about 6 hours to about 100 days. A more preferred temperature range is from about 150° F to about 400° F with the amount of time at a temperature in such range being from about 6 hours to about 80 days.

The digestion of the gel particles is carried out until crystals form. The solid product is separated from the reaction medium, as by cooling the whole to room temperaure, filtering and water washing. The crystalline product is dried, e.g at 230° F, for from about 8 to 24 hours.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

TABLE 3

|  | Broad | Preferred |
|---|---|---|
| $R^+$ | 0.2 – 1.0 | 0.3 – 0.9 |
| $\dfrac{R^+ + M^+}{OH^-/SiO_2}$ | 0.05 – 0.5 | 0.07 – 0.49 |
| $H_2O/OH^-$ | 41 – 500 | 100 – 250 |
| $SiO_2/Al_2O_3$ | 8.8 – 200 | 12 – 60 | wherein R is an organic nitrogen-containing cation derived from a 2-(hydroxyalkyl) trialkylammonium compound and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperaure of from about 90° F to about 400° F for a period of time of from about 6 hours to about 100 days. A more preferred temperature range is from about 150° F to about 400° F with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F for from about 8 to 24 hours.

For the disproportionation process of this invention the suitable zeolite catalyst is employed in combination with a support or binder material such as, for example, a porous inorganic oxide support or a clay binder. Non-limiting examples of such binder materials include alumina, zirconia, silica, magnesia, thoria, titania, boria and combinations therof, generally in the form of dried inorganic oxide gels and gelatinous precipitates. Suitable clay materials include, by way of example, bentonite and kieselguhr. The relative proportion of suitable crystalline aluminosilicate zeolite of the total composition of catalyst and binder or support may vary widely with the zeolite content ranging from between about 30 to about 90 percent by weight and more usually in the range of about 50 to about 80 percent by weight of the composition.

Operating conditions employed in the process of the present invention are critical. Such conditions as temperature, pressure, space velocity, molar ratio of the reactants, hydrogen to hydrocarbon mole ratio, and the presence of inert diluents will have important affects on the process.

The process of this invention is conducted such that disproportionation of toluene is carried out in the vapor-phase by contact in a reaction zone, such as, for example, a fixed bed of catalyst composition, under disproportionation effective conditions, said catalyst composition being characterized, as synthesized, as comprising the above-defined zeolite which has been hydrogen, hydrogen precusor and/or non-noble Group VIII metal exchanged. The effluent is separated and distilled to remove desired product, such as benzene and xylene, and unreacted reactant, i.e., toluene, is recycled for further reaction.

By the present process toluene is converted to aromatic concentrates of high value, e.g., xylene and benzene. This process may be conducted in either batch or fluid bed operation with attendant benefits of either operation readily obtainable.

In the process of this invention, the toluene charge is preferably dried in a manner which will minimize the water entering the reaction employed. Means known in the art suitable for drying the toluene charge to the present process are numerous, including percolation through silica gel, molecular sieves or other suitable substance or use of liquid charge dryers.

In a typical embodiment of the present process, optimum toluene conversion is found to be from about 40 weight percent to about 50 weight percent. Yield of $C_5^-$ products and ring losses in such an embodiment appear to increase at conversion above about 40 percent and xylene yields begin to decrease when toluene conversion exceeds about 50 weight percent.

Considering this vapor-phase disproportionation of toluene, the first stage feed is heated to a temperature within the range of about 650° F to about 1100° F at a pressure within the range of about atmospheric to about 100 psig. Preferred inlet temperatures for the process of the present invention fall within the range of about 850° F to about 1000° F and preferred pressures fall within the range of about 400 psig to about 800 psig. Preferred hydrogen to hydrocarbon mole ratios are 0 to about 3, with a particularly preferred range of 0 to about 1.5. This process shows exceptional economic advantage even at a hydrogen to hydrocarbon mole ratio of 0.

The following specific examples will serve to illustrate the process of the present invention, without unduly limiting same.

EXAMPLE 1

A catalyst for use in the present process was prepared by first preparing the following separate solutions:

Silicate Solution
90.0 lb. Q-Brand Sodium Silicate (8.9 wt. % $Na_2O$, 28.7 wt. % $SiO_2$ and 62.4 wt. % $H_2O$)
52.6 lb. $H_2O$
118 g. Daxad 27 (dispersant comprised of a sodium salt of polymerized, substituted benzoid alkyl sulfonic acids combined with an inert inorganic suspending agent)
Acid Solution
1430 g. $Al_2(SO_4)_3 \cdot xH_2O$ (M.W. = 595)
3440 g. $H_2SO_4$
3890 G. NaCl
54 lb $H_2O$
Organics Solution
2780 g. tri-n-propylamine
2390 g. n-propyl bromide
4590 g. MEK The silicate solution and acid solution were mixed in a mixing nozzle to form a gel which was discharged into a 30 gallon autoclave to which 1180 g. of $H_2O$ had been previously added. The gel was whipped by agitation and 2840 g. of NaCl was added and thoroughly blended. The agitation was stopped and the organics solution was added as a layer on top of the gel. The autoclave was sealed and heated to 220° F without agitation and held there for 14–15 hours to prereact the organics. At the end of prereaction period the agitation was commenced at 90 RPM to start the initial crystallization period. After about 75–80 hours the temperature was raised to 320° F and held there for about 3 hours to complete crystallization. The excess or unreacted organics were flashed off and the contents of the autoclave were cooled and discharged. The product was analyzed by X-ray diffraction and shown to be 100% crystallinity ZSM-5 based upon a standard sample. Chemical analysis of the thoroughly washed crystalline product was:

|  | % Wt. | Mole Ratio |
|---|---|---|
| $Al_2O_3$ | 2.21 | 1.0 |
| $SiO_2$ | 94.9 | 72.8 |
| Na | 0.81 | — |
| $Na_2O$ | — | 0.82 |
| N | 0.67 | 2.48 |
| C | 8.2 | 35.6 |

After thorough washing and drying at about 250° F, the zeolite was mixed with alpha monohydrate and water (65% zeolite, 35% alumina binder on an ignited basis) and extruded to form 1/16 inch pellets.

After drying the pellets, the zeolite was transformed into the catalytic form by the following steps:
1. Precalcination in a 100% $N_2$ atmosphere (3 volumes $N_2$/volume of catalyst/minute) for 3 hours at 1000° F and atmospheric pressure employing a programmed heat up rate of 5° F/min. to 1000° F from ambient.
2. Ion exchange with 1 $NH_4NO_3$ at room temperature for 1 hour using 5 cc of exchange solution per grams of dry extrudate. Ion exchange repeated and catalyst washed with water for 15 minutes and dried.
3. Ion exchange with 1 N Ni $(NO_4)_3$ at 190° F for 4 hours using 5 cc of exchange solution per gram of dry extrudate. Extrudate then washed with water for 4 hours and dried.
4. Calcination in a 100% air atmosphere (3 volumes air/volume of catalyst/minute) for 3 hours at 1000° F and atmospheric pressure employing a programmed heat up rate of 5° F/min to 100° F from ambient.

The final product was analyzed and found to contain 1.03 wt. % Ni and less then 0.01 wt. % Na.

EXAMPLES 2–4

The extrudate catalyst composition of Example 1 was crushed to 28 × 60 - mesh particles and 1.7 grams (2.8 cc) thereof was diluted with 7.2 cc of 28 × 48 - mesh tubular alumina. The resulting catalyst composition was then heated at 900° F under a pressure of 400 psig with 162 cc/minute of hydrogen passed therethrough for one hour.

The treated catalyst composition was then placed in a closed pressure reaction vessel as a fixed bed and a charge of toluene was continuously fed thereto (after being perked through silica gel) at a rate which maintained the WHSV at 1.4. The reaction pressure was maintained at 600 psig and hydrogen was supplied to the reaction vessel to maintain a hydrogen to hydrocarbon mole ratio of 4:1. The initial temperature of the experiment was 747° F and the initial material balance was 96.8. Examples 2 through 4 were established by periodically measuring reaction temperature (changed in Examples 3 and 4), reaction material balance and analyzing reaction product. A summary of these experiments appears in Table 4 below:

TABLE 4
Toluene Disproportionation in Examples 2–4

| Example No. | 2 | 3 | 4 |
|---|---|---|---|
| Material Balance | 96.8 | 97.8 | 100.4 |
| Temperature, ° F | 747 | 773 | 800 |
| Time on Stream, hours | 3.1 | — | — |
| Product Distribution, weight percent | | | |
| Methane | 0.1 | — | 0.003 |
| Ethane | 0.9 | 0.2 | 0.3 |
| Propane | 2.7 | 0.7 | 1.1 |
| Isobutane | 0.5 | 0.1 | 0.1 |
| n-Butane | 0.6 | 0.1 | 0.1 |
| $C_4$ Olefins | 0.03 | — | — |
| Isopentane | 0.2 | 0.01 | — |
| n-Pentane | 0.04 | — | — |
| 3-Methylpentane | Trace | — | — |
| n-Hexane | Trace | — | — |
| Methyl-cyclohexane | Trace | — | — |
| Benzene | 11.6 | 13.0 | 17.7 |
| $C_7$ Paraffins | 0.1 | 0.04 | — |
| Toluene | 65.8 | 68.0 | 56.6 |
| $C_8$ Paraffins | 0.05 | — | — |
| p- and m-xylenes | 12.0 | 12.6 | 16.0 |
| o-xylene | 3.3 | 3.4 | 5.2 |
| $C_9$ Aromatics | 1.7 | 1.6 | 2.8 |
| $C_{10}^+$ Aromatics | 0.5 | 0.2 | — |
| Toluene Reacted, weight percent | 34.2 | 32.0 | 43.4 |

EXAMPLES 5a–5d

An extrudate catalyst composition was prepared as in Example 1 except that it was not nickel nitrate exchanged. Instead, it was ion exchanged by treatment four times for 1 hour each at room temperature with 5 cc of 5 percent aqueous ammonium chloride per gram of ZSM-5. The extrudate was prepared and treated essentially as in Examples 2–4 and was placed in a closed pressure reaction vessel as a fixed bed. A charge of toluene was continuously fed to the reaction vessel (after being perked through silica gel) at a rate which maintained the WHSV at 1.4. The reaction pressure was maintained at 610 psig for Examples 5a–5c and at 605 psig for Example 5d. No hydrogen was supplied to the reaction vessel. The initial temperature of the experiment was 700° F and the initial material balance was 95.8. Examples 5a through 5d were established by periodically measuring reaction temperature (changed for Examples 5b–5d), reaction material balance and analyzing reaction products. A summary of these experiments appear in Table 5 below:

TABLE 5
Toluene Disproportionation in Examples 5a–5d
With a Hydrogen/Hydrocarbon Mole Ratio of Zero

| Example No. | 5a | 5b | 5c | 5d |
|---|---|---|---|---|
| Material Balance | 95.8 | 101.2 | 100.6 | 100.1 |
| Temperature, ° F | 700 | 752 | 797 | 810 |
| Time on Stream, hours | 20.1 | 41.8 | 64.6 | 88.8 |
| Product Distribution, weight percent | | | | |
| Ethane | 0.002 | 0.002 | 0.08 | 0.03 |
| Propane | 0.08 | 0.19 | 0.16 | 0.17 |
| Benzene | 5.1 | 12.6 | 17.9 | 17.5 |
| Toluene | 87.7 | 71.8 | 58.6 | 60.2 |
| $C_8$ Paraffins | 0.01 | — | — | — |
| p- and m-xylenes | 5.01 | 9.9 | 15.1 | 15.1 |
| o-xylene | 1.3 | 2.9 | 4.1 | 4.3 |
| $C_9$ Aromatics | 0.5 | 1.4 | 2.1 | 1.7 |
| $C_{10}^+$ Aromatics | 0.4 | 1.1 | 1.8 | 1.1 |
| Toluene Reacted, weight percent | 12.3 | 28.2 | 41.4 | 39.8 |

EXAMPLES 6–18

An extrudate catalyst composition prepared as in Example 1 was treated as in Examples 2–4 and was placed in a closed pressure reaction vessel as a fixed bed. A charge of toluene was continuously fed to the reaction vessel (after being perked through silica gel) at a ratio which maintained the WHSV at 2.0. The reaction pressure was maintained at 500 psig. Hydrogen was supplied to the reaction vessel to maintain a hydrogen/hydrocarbon mole ratio of 4/1. The reaction temperature for Examples 6–14 was maintained at about 800° F and for Examples 15–18 at about 900° F. The separate examples were established by periodically measuring reaction temperature, material balance and analyzing reaction products. A summary of these experiments appears in Tables 6A, 6B, 6C, 6D and 6E, hereinafter presented.

TABLE 6-A
Toluene Disproportionation in Examples 6–8

| Example No. | 6 | 7 | 8 |
|---|---|---|---|
| Temperature, ° F | 800 | 800 | 800 |
| Pressure, psig | 500 | 500 | 500 |
| WHSV | 2.00 | 2.00 | 2.00 |
| Hydrogen/Hydrocarbon, mole ratio | 4/1 | 4/1 | 4/1 |
| Material Balance | 100.44 | 99.30 | 98.49 |
| Time on Stream, hours | 2.25 | 22.50 | 50.25 |
| Product Distribution, weight percent | | | |
| Methane | .09 | .01 | .00 |
| Ethane | 2.17 | .94 | .70 |
| Propane | 5.77 | 2.32 | 1.70 |
| Butanes + $C_4$ Olefins | 1.55 | .61 | .41 |
| Pentanes | .21 | .07 | .04 |
| Benzene | 11.41 | 12.16 | 11.02 |
| $C_7$ Paraffins | .06 | .05 | .07 |
| Toluene | 60.57 | 65.93 | 70.40 |
| $C_8$ Paraffins | .08 | .02 | .00 |
| p- and m-xylenes | 12.88 | 12.84 | 11.34 |
| o-xylene | 3.57 | 3.74 | 3.08 |
| $C_9$ Aromatics | 1.41 | 1.05 | .94 |
| $C_{10}^+$ Aromatics | .14 | .08 | .07 |
| Naphthalenes | .00 | .10 | .01 |
| Toluene Reacted, weight percent | 39.43 | 34.07 | 29.60 |

TABLE 6-B
Toluene Disproportionation in Examples 9–11

| Example No. | 9 | 10 | 11 |
|---|---|---|---|
| Temperature, ° F | 802 | 799 | 802 |
| Pressure, psig | 500 | 500 | 500 |
| WHSV | 2.00 | 2.00 | 2.00 |
| Hydrogen/Hydrocarbon, mole ratio | 4/1 | 4/1 | 4/1 |
| Material Balance | 99.78 | 98.44 | 96.15 |
| Time on Stream, hours | 118.25 | 142.50 | 166.50 |
| Product Distribution, weight percent | | | |
| Methane | .00 | .00 | .00 |
| Ethane | .47 | .40 | .37 |
| Propane | 1.20 | 1.01 | .96 |
| Butanes + $C_4$ Olefins | .26 | .22 | .21 |
| Pentanes | .02 | .00 | .02 |
| Benzene | 11.24 | 11.06 | 11.07 |
| $C_7$ Paraffins | .04 | .00 | .06 |
| Toluene | 71.29 | 72.07 | 72.43 |
| $C_8$ Paraffins | .03 | .02 | .01 |
| p- and m-xylenes | 11.29 | 11.07 | 10.90 |
| o-xylene | 3.08 | 3.02 | 2.96 |
| $C_9$ Aromatics | .88 | .86 | .81 |
| $C_{10}^+$ Aromatics | .07 | .07 | .06 |
| Naphthalenes | .01 | .01 | .01 |
| Toluene Reacted, weight percent | 28.71 | 27.93 | 27.57 |

TABLE 6C
Toluene Disproportionation in Examples 12–14

| Example No. | 12 | 13 | 14 |
|---|---|---|---|
| Temperature, ° F | 800 | 800 | 801 |
| Presssure, psig | 500 | 500 | 500 |
| WHSV | 2.00 | 2.00 | 2.00 |
| Hydrogen/Hydrocarbon, mole ratio | 4/1 | 4/1 | 4/1 |
| Material Balance | 97.98 | 100.71 | 99.09 |
| Time on Stream, hours | 190.50 | 214.50 | 290.25 |
| Product Distribution, weight percent | | | |
| Methane | .00 | .00 | .00 |
| Ethane | .32 | .37 | .38 |
| Propane | .84 | .93 | .91 |
| Butanes + $C_4$ Olefins | .20 | .18 | .19 |
| Pentanes | .02 | .01 | .02 |
| Benzene | 10.97 | 10.91 | 11.27 |
| $C_7$ Paraffins | .01 | .01 | .03 |
| Toluene | 73.10 | 72.60 | 71.79 |
| $C_8$ Paraffins | .00 | .00 | .05 |
| p- and m-xylenes | 11.00 | 10.98 | 11.23 |
| o-xylene | 2.99 | 2.98 | 3.07 |
| $C_9$ Aromatics | .37 | .84 | .83 |
| $C_{10}^+$ Aromatics | .04 | .04 | .06 |
| Naphthalenes | .01 | .01 | .01 |
| Toluene Reacted, weight percent | 26.90 | 27.40 | 28.21 |

TABLE 6D
Toluene Disproportionation in Examples 15–16

| Example No. | 15 | 16 |
|---|---|---|
| Temperature, ° F | 896 | 899 |
| Pressure, psig | 500 | 500 |

TABLE 6D-continued

Toluene Disproportionation in Examples 15-16

| Example No. | 15 | 16 |
|---|---|---|
| WHSV | 2.00 | 2.00 |
| Hydrogen/Hydrocarbon, mole ratio | 4/1 | 4/1 |
| Material Balance | 98.74 | 98.56 |
| Time on Stream, hours | 314.50 | 338.25 |
| Product Distribution, weight percent | | |
| Methane | .08 | .09 |
| Ethane | 1.67 | 1.61 |
| Propane | 1.61 | 1.51 |
| Butanes +$C_4$ Olefins | .08 | .08 |
| Pentanes | .00 | .00 |
| Benzene | 23.14 | 23.40 |
| $C_7$ Paraffins | .05 | .03 |
| Toluene | 47.67 | 47.21 |
| $C_8$ Paraffins | .03 | .09 |
| p- and m-xylenes | 17.61 | 17.71 |
| o-xylene | 5.09 | 5.17 |
| $C_9$ Aromatics | 2.46 | 2.54 |
| $C_{10}^+$ Aromatics | .14 | .11 |
| Naphthalenes | .02 | .03 |
| Toluene Reacted, weight percent | 52.33 | 52.79 |

TABLE 6E

Toluene Disproportionation in Examples 17-18

| Example No. | 17 | 18 |
|---|---|---|
| Temperature, °F | 900 | 901 |
| Pressure, psig | 500 | 500 |
| WHSV | 2.00 | 2.00 |
| Hydrogen/Hydrocarbon, mole ratio | 4/1 | 4/1 |
| Material Balance | 97.94 | 97.50 |
| Time on Stream, hours | 362.25 | 386.25 |
| Product Distribution, weight percent | | |
| Methane | .06 | .09 |
| Ethane | 1.53 | 1.71 |
| Propane | 1.42 | 1.48 |
| Butanes + $C_4$ Olefins | .08 | .09 |
| Pentanes | .00 | .00 |
| Benzene | 23.54 | 23.86 |
| $C_7$ Paraffins | .06 | .00 |
| Toluene | 47.27 | 46.96 |
| $C_8$ Paraffins | .11 | .10 |
| p- and m-xylenes | 17.72 | 17.57 |
| o-xylene | 5.17 | 5.12 |
| $C_9$ Aromatics | 2.52 | 2.49 |
| $C_{10}$ + Aromatics | .09 | .09 |
| Naphthalenes | .05 | .05 |
| Toluene Reacted, weight percent | 52.73 | 53.04 |

EXAMPLES 19-23

A quantity of catalyst material as used in Examples 6-18 was placed in a closed pressure reaction vessel. A charge of toluene was continuously fed to the reaction vessel (after being perked through silica gel) at a ratio which maintained the WHSV at 2.0. The reaction pressure and temperature were maintained at 500 psig and about 800° F, respectively. No hydrogen was supplied to the reaction vessel. The separate examples were established by periodically measuring reaction temperature, material balance and analyzing reaction products. A summary of these experiments appears in Tables 7A and 7B hereinafter presented.

TABLE 7A

Toluene Disproportionation in Examples 19-21 With a Hydrogen/Hydrocarbon Mole Ratio of Zero

| Example No. | 19 | 20 | 21 |
|---|---|---|---|
| Temperature, °F | 800 | 800 | 800 |
| Pressure, psig | 500 | 500 | 500 |
| WHSV | 2.00 | 2.00 | 2.00 |
| Hydrogen/Hydrocarbon, mole ratio | 0 | 0 | 0 |
| Material Balance | 87.20 | 101.17 | 99.87 |
| Time on Stream, hours | 2.25 | 22.75 | 50.25 |
| Product Distribution, weight percent | | | |
| Methane | .00 | .00 | .00 |
| Ethane | .07 | .00 | .00 |
| Propane | .21 | .09 | .08 |
| Butanes +$C_4$ Olefins | .00 | .00 | .00 |
| Pentanes | .00 | .00 | .00 |
| Benzene | 17.17 | 16.38 | 15.87 |
| $C_7$ Paraffins | .05 | .03 | .00 |
| Toluene | 61.63 | 61.89 | 63.42 |
| $C_8$ Paraffins | .17 | .10 | .12 |
| p- and m-xylenes | 14.39 | 14.78 | 14.21 |
| o-xylene | 3.96 | 4.08 | 3.91 |
| $C_9$ Aromatics | 1.45 | 1.19 | 1.05 |
| $C_{10}^+$ Aromatics | .06 | .06 | .03 |
| Naphthalenes | .33 | .32 | .48 |
| Toluene Reacted, weight percent | 38.37 | 38.11 | 36.58 |

TABLE 7B

Toluene Disproportionation in Examples 22-23 With a Hydrogen/Hydrocarbon Mole Ratio of Zero

| Example No. | 22 | 23 |
|---|---|---|
| Temperature, °F | 801 | 801 |
| Pressure, psig | 500 | 500 |
| WHSV | 2.00 | 2.00 |
| Hydrogen/Hydrocarbon, mole ratio | 0 | 0 |
| Material Balance | 99.35 | 99.26 |
| Time on Stream, hours | 70.75 | 146.75 |
| Product Distribution, weight percent | | |
| Methane | .00 | .00 |
| Ethane | .00 | .00 |
| Propane | .04 | .06 |
| Butanes +$C_4$ Olefins | .00 | .00 |
| Pentanes | .00 | .00 |
| Benzene | 15.48 | 15.39 |
| $C_7$ Paraffins | .00 | .04 |
| Toluene | 64.10 | 63.91 |
| $C_8$ Paraffins | .06 | .12 |
| p- and m-xylenes | 14.04 | 14.29 |
| o-xylene | 3.87 | 3.89 |
| $C_9$ Aromatics | 1.04 | .92 |
| $C_{10}$+ Aromatics | .02 | .03 |
| Naphthalenes | .31 | .30 |
| Toluene Reacted, weight percent | 35.90 | 36.09 |

EXAMPLE 24

Ninety grams of NaY zeolite were exchanged with 1 N $NH_4NO_3$ solution. Ten milliliters of solution was used per gram of zeolite. A total of three one-hour exchanges were carried out to reduce sodium content in the zeolite to 0.19% by weight. After thorough washing and drying, the $NH_4Y$ zeolite sample was exchanged with a solution of 6.8 grams $Ni(NO_3)_2.6H_2O$ in 680 ml of water, stirred at ambient temperature for three hours. The same was again filtered, washed and dried. Highly pure alumina treated as in Example 1 was added to the dried sample to form a 65% zeolite and 35% alumina mixture on a dry solids basis. The mixture and 54 ml of water were mulled for 30 minutes, then were extruded through a 1/16 inch die plate using a hydraulic extruder. The dried extrudates were calcined at 1000° F for 3 hours with 3 volumes of air flowing per volume of catalyst per minute. The final catalyst was analyzed and found to contain 1.2 weight percent Ni and 0.16 weight percent Na and to have a particle density of 1.0 gram/cc.

EXAMPLES 25 and 26

A quantity of the extrudate catalyst composition of Example 24 was treated as in Examples 2-4 and was placed in a closed pressure reaction vessel as a fixed bed. A charge of toluene was continuously fed to the reactive vessel (after being perked through silica gel) at a rate which maintained the WHSV at 2.0. The reaction pressure was maintained at 500 psig. Hydrogen was supplied to the reaction vessel to maintain a hydrogen/hydrocarbon mole ratio of 4/1. The reaction temperature was maintained at about 800° F and the separate examples were established by periodically measuring reaction conditions and analyzing reaction products. A summary of these experiments appears in Table 8A, hereinafter presented.

TABLE 8A
Toluene Disproportionation in Examples 25-26

| Example No. | 25 | 26 |
|---|---|---|
| Temperature, ° F | 809 | 800 |
| Pressure, psig | 500 | 500 |
| WHSV | 2.00 | 2.00 |
| Hydrogen/Hydrocarbon, mole ratio | 4/1 | 4/1 |
| Material Balance | 100.09 | 99.32 |
| Time on Stream, hours | 2.25 | 69.25 |
| Product Distribution, weight percent | | |
| Methane | .49 | .00 |
| Ethane | 1.37 | .46 |
| Propane | 6.97 | 2.10 |
| Butanes +$C_4$ Olefins | 6.84 | .70 |
| Pentanes | 2.14 | .09 |
| Benzene | 13.86 | 3.16 |
| $C_7$ Paraffins | 5.14 | .51 |
| Toluene | 36.84 | 88.06 |
| $C_8$ Paraffins | .87 | .15 |
| p- and m-xylenes | 13.61 | 3.36 |
| o-xylene | 3.69 | .09 |
| $C_9$ Aromatics | 2.79 | .74 |
| $C_{10}$+ Aromatics | .71 | .16 |
| Naphthalenes | .00 | .00 |
| Toluene Reacted, weight percent | | |
| | 63.16 | 11.94 |

EXAMPLES 27 and 28

The same procedure and catalyst as for Examples 25 and 26 was followed for Examples 27 to 28, except that no hydrogen was supplied to the reaction vessel. A summary of these experiments appears in Table 8B, hereinafter presented.

TABLE 8B
Toluene Disproportionation in Examples 27-28
With a Hydrogen/Hydrocarbon Mole Ratio of Zero

| Example No. | 27 | 28 |
|---|---|---|
| Temperature, ° F | 801 | 798 |
| Pressure, psig | 500 | 500 |
| WHSV | 2.00 | 2.00 |
| Hydrogen/Hydrocarbon, mole ratio | 0 | 0 |
| Material Balance | 75.98 | 98.28 |
| Time on Stream, hours | 2.25 | 21.25 |
| Product Distribution, weight percent | | |
| Methane | .00 | .00 |
| Ethane | .00 | .00 |
| Propane | .00 | .00 |
| Butanes +$C_4$ Olefins | .00 | .00 |
| Pentanes | .00 | .00 |
| Benzene | 4.10 | .21 |
| $C_7$ Paraffins | .02 | .00 |
| Toluene | 90.70 | 98.91 |
| $C_8$ Paraffins | .00 | .08 |
| p- and m-xylenes | 3.59 | .09 |
| o-xylene | .81 | .03 |
| $C_9$ Aromatics | .22 | .01 |
| $C_{10}$+ Aromatics | .03 | .00 |
| Naphthalenes | .00 | .00 |
| Toluene Reacted, weight percent | | |
| | 9.30 | 1.09 |

EXAMPLE 29

A quantity of ZSM-4 zeolite was prepared by first preparing the following two solutions:

| | Quantity, pounds |
|---|---|
| Silicate solution | |
| Q-Brand water glass (as in Example 1) | 106 |
| NaOH | 14.2 |
| TMACl (50% soln) | 5.6 |
| Ice | 65.2 |
| Acid alum solution | |
| $Al_2(SO_4)_3 \cdot xH_2O$ | 17.9 |
| $H_2SO_4$ | 5.03 |
| $H_2O$ | 48.4 |

The silicate and acid alum solutions were charged into 30 gallon autoclave simultaneously to form gel. 19.49 pounds of NaCl was added to the gel. The mixture was whipped for 1 hour at 250 rpm agitation. The homogeneous gel was crystallized at 219° F for 66 hours at 90 rpm agitation. The crystallinity of final product was 135% ZSM-4. The zeolite was separated from mother liquor by filtration and followed by washing and drying at 230° F. It had the following analysis:

| | Weight Percent |
|---|---|
| $Al_2O_3$ | 16.6 |
| $SiO_2$ | 73.5 |
| Na | 5.9 |
| N | 0.89 |
| C | 3.34 |
| Ash | 83.8 |

A mixture of 65% crystals of above formed ZSM-4 and 35% highly pure alumina was mulled together with added water and was extruded on the hydraulic extruder through a 1/16 inch die plate. The extrudate was then transformed into catalytic form by the following steps:

a. Precalcining in a 100% $N_2$ atmosphere for 3 hours at 1000° F, employing a programmed heat-up rate of 5° F/minute to 1000° F from ambient;

b. Ion exchange with 1N $NH_4NO_3$ at room temperature for 1 hour using 5 ml of exchange solution per gram of dry extrudate;

c. Washing the extrudate with $H_2O$, and exchanging again with 1 N Ni $(NO_3)_2$ solution for 4 hours at 180° F using 5 ml of exchange solution per gram of dry extrudate;

d. Washing the extrudate with water to Ni ion free;

e. Calcining in air for 3 hours at 1000° F employing a programmed heat-up rate of 5° F/minute to 1000° F from ambient.

The final catalyst was analyzed and found to contain 1.0 weight percent Ni and 0.03 percent Na and to have a particle density of 1.16 grams/cc.

EXAMPLES 30 – 35

The same procedure as for Examples 25 and 26 was followed for Examples 30-35 with the catalyst of Example 29, except that no hydrogen was supplied to the reaction vessel for Example 30. A summary of these experiments appears in Tables 9A and 9B, hereinafter presented.

TABLE 9A

Toluene Disproportionation in Examples 30–32

| Example No. | 30 | 31 | 32 |
|---|---|---|---|
| Temperature, °F | 799 | 801 | 801 |
| Pressure, psig | 500 | 500 | 500 |
| WHSV | 2.00 | 2.00 | 2.00 |
| Hydrogen/Hydrocarbon, mole ratio | 0 | 4/1 | 4/1 |
| Material Balance | 106.04 | 99.87 | 99.76 |
| Time on Stream, hours | 3.20 | 1.20 | 21.20 |
| Product Distribution, weight percent | | | |
| Methane | .00 | .70 | .18 |
| Ethane | .00 | 4.07 | 1.57 |
| Propane | .00 | 13.46 | 5.24 |
| Butanes + $C_4$ Olefins | .00 | 3.70 | 1.09 |
| Pentanes | .00 | .64 | .10 |
| Benzene | 3.10 | 14.72 | 19.17 |
| $C_7$ Paraffins | .00 | .00 | .00 |
| Toluene | 94.63 | 32.64 | 42.76 |
| $C_8$ Paraffins | .00 | .12 | .09 |
| p- and m-xylenes | 1.76 | 18.81 | 19.77 |
| o-xylene | .51 | 5.05 | 5.46 |
| $C_9$ Aromatics | .00 | 5.78 | 4.24 |
| $C_{10}$+ Aromatics | .00 | .30 | .08 |
| Naphthalenes | .00 | .00 | .24 |
| Toluene Reacted, weight percent | 5.37 | 67.36 | 57.24 |

TABLE 9B

Toluene Disproportionation in Examples 33–35

| Example No. | 33 | 34 | 35 |
|---|---|---|---|
| Temperature, °F | 799 | 798 | 800 |
| Pressure, psig | 500 | 500 | 500 |
| WHSV | 2.00 | 2.00 | 2.00 |
| Hydrogen/Hydrocarbon, mole ratio | 4/1 | 4/1 | 4/1 |
| Material Balance | 99.95 | 100.15 | 98.81 |
| Time on Stream, hours | 48.65 | 69.20 | 141.20 |
| Product Distribution, weight percent | | | |
| Methane | .04 | .01 | .00 |
| Ethane | .73 | .43 | .17 |
| Propane | 2.26 | 1.34 | .57 |
| Butanes + $C_4$ Olefins | .31 | .15 | .05 |
| Pentanes | .01 | .00 | .01 |
| Benzene | 18.46 | 16.69 | 13.77 |
| $C_7$ Paraffins | .00 | .00 | .00 |
| Toluene | 54.00 | 59.55 | 66.45 |
| $C_8$ Paraffins | .14 | .07 | .04 |
| p- and m-xylenes | 17.04 | 15.69 | 12.95 |
| o-xylene | 4.94 | 4.58 | 3.50 |
| $C_9$ Aromatics | 2.08 | 1.48 | 1.69 |
| $C_{10}$+ Aromatics | .00 | .00 | .19 |
| Napthalenes | .00 | .00 | .30 |
| Toluene Reacted, weight percent | 46.00 | 40.45 | 33.55 |

EXAMPLE 36

A 195.1 gram sample of synthetic H-mordenite (Zeolon 100H) was exchanged with a solution 14.53 grams Ni (NO$_3$)$_2$. 6H$_2$O in 975 ml of water. After 2 hours at 160° F with stirring, the sample was filtered, washed and dried. The sample, added highly pure alumina and water were mulled for about 30 minutes. The composite was then extruded through a 1/16 inch die plate using a hydraulic extruder. It was then calcined for 3 hours at 1000° F with 3 volumes of air per volume of catalyst per minute. The final catalyst was analyzed and was found to contain 1.1 weight percent Ni and 0.15 weight percent Na and to have a particle density of 1.07 grams/cc.

EXAMPLES 37–39

The same procedure as for Examples 25 and 26 was followed for Examples 37–39 with the catalyst of Example 36, except that no hydrogen was supplied to the reaction vessel for Example 39. A summary of these experiments appears in Table 10, hereinafter presented.

TABLE 10

Toluene Disproportionation in Examples 37–39

| Example No. | 37 | 38 | 39 |
|---|---|---|---|
| Temperature, °F | 800 | 798 | 798 |
| Pressure, psig | 500 | 465 | 500 |
| WHSV | 2.00 | 2.00 | 2.00 |
| Hydrogen/Hydrocarbon, mole ratio | 4/1 | 4/1 | 0 |
| Material Balance | 92.73 | 92.49 | 89.00 |
| Time on Stream, hours | 2.25 | 97.00 | 1.75 |
| Product Distribution, weight percent | | | |
| Methane | .05 | .00 | .00 |
| Ethane | .87 | .14 | .02 |
| Propane | 3.81 | .49 | .00 |
| Butanes + $C_4$ Olefins | .39 | .00 | .00 |
| Pentanes | .00 | .00 | .00 |
| Benzene | 24.19 | 10.26 | 3.95 |
| $C_7$ Paraffins | .00 | .00 | .00 |
| Toluene | 41.52 | 77.15 | 92.23 |
| $C_8$ Paraffins | .05 | .04 | .00 |
| p- and m-xylenes | 19.58 | 9.49 | 3.27 |
| o-xylene | 5.41 | 2.30 | .53 |
| $C_9$ Aromatics | 3.90 | .13 | .00 |
| $C_{10}$+ Aromatics | .14 | .00 | .00 |
| Naphthalenes | .08 | .00 | .00 |
| Toluene Reacted, weight percent | 58.48 | 22.85 | 7.77 |

EXAMPLE 40

A 180 gram sample of REY zeolite was exchanged with a solution of 15 grams of Ni(NO$_3$)$_2$. 6H$_2$O and 1400 grams of water for 2 hours at ambient temperature with stirring. At the end of exchange, the sample was filtered, thoroughly washed and dried. To the dried sample, water and highly pure alumina were added as in Example 1 and the mixture was mulled into an extrudable means. Extrusion was accomplished on a hydraulic extruder through a 1/16 inch die plate. The dried extrudate was finally air calcined at 1000° F for 3 hours with 3 volumes of air per volume of catalyst per minute. The final catalyst was found to contain 0.58 weight percent Ni. The particle density and crushing strength were found to be 1.022 grams/cc and 44 lb/inch, respectively.

EXAMPLES 41–43

The same procedure as for Examples 25 and 26 was followed for Examples 41–43 with the catalyst of Example 40, except that no hydrogen was supplied to the reaction vessel for Example 43. A summary of these experiments appear in Table 11, hereinafter presented.

TABLE 11

Toluene Disproportionation in Examples 41–43

| Example No. | 41 | 42 | 43 |
|---|---|---|---|
| Temperature, °F | 800 | 800 | 800 |
| Pressure, psig | 500 | 500 | 500 |
| WHSV | 2.00 | 2.00 | 2.00 |
| Hydrogen/Hydrocarbon, mole ratio | 4/1 | 4/1 | 0 |
| Material Balance | 98.19 | 100.40 | 109.38 |
| Time on Stream, hours | 1.25 | 21.25 | 3.00 |
| Product Distribution, weight percent | | | |
| Methane | .02 | .00 | .00 |
| Ethane | .64 | .20 | .00 |
| Propane | 2.31 | .61 | .00 |
| Butanes + $C_4$ Olefins | 2.42 | .08 | .00 |
| Pentanes | .82 | .02 | .00 |
| Benzene | 14.80 | 2.21 | 2.03 |
| $C_7$ Paraffins | 3.20 | .32 | .01 |
| Toluene | 45.52 | 92.94 | 94.89 |
| $C_8$ Paraffins | .99 | .16 | .00 |
| p- and m-xylenes | 16.80 | 2.36 | 1.94 |
| o-xylene | 4.67 | .59 | .41 |
| $C_9$ Aromatics | 5.38 | .30 | .09 |
| $C_{10}$ + Aromatics | .90 | .07 | .01 |
| Naphthalenes | .00 | .00 | .00 |
| Toluene Reacted, weight percent | | | |

TABLE 11-continued

Toluene Disproportionation in Examples 41–43

| Example No. | 41 | 42 | 43 |
|---|---|---|---|
|  | 54.48 | 7.06 | 5.11 |

EXAMPLES 44–62

In order to more fully evaluate the performance of the present process and to exemplify beneficial selectivity of conversion to para-xylene, it was conducted on a large scale with charge rate in barrels/day, hydrogen/hydrocarbon mole ratio, average reactor temperature in ° F, liquid hourly space velocity in hr$^{-1}$, toluene conversion in weight percent, para-xylene production in MLBS/hour and total xylene production in MLBS/hour measured periodically. From the data generated by the large scale process, approach to equilibrium was calculated as being (weight % para-xylene of total xylenes produced)/(para-xylene equilibrium concentration at the average reactor temperature). The para-xylene -equilibrium concentration as a function of reactor temperature was determined according to *The Chemical Thermodynamics of Organic Compounds* by Stull, Westrum and Sinke, published in 1969 by Wiley.

The reactor had a volume of 800 cubic feet and contained 15 MLBS of catalyst prepared as in Example 1. The toluene charge was supplied to the reactor inlet at the top thereof through a diffuser having an inside diameter of 394 mm with holes approximately every 10 mm. The toluene charge then passed through approximately 900 mm of inert chips, an 8 mm screen, the catalyst for a distance of approximately 4770 mm and then approximately 1400 mm of inert chips. Thermocouples were placed in the catalyst at distances of about 4000 mm, 5500 mm and 7000 mm from the extreme top of the reactor.

The data generated by the process and calculated values for approach to equilibrium for para-xylene are presented below in Table 12. It is observed that the approach to equilibrium is consistently greater than 100, indicating selectivity to para-xylene at the expense of some other, less desirable product. Conversion remained high throughout the test.

TABLE 12

| Ex. | Days On Stream | Charge B/D | H$_2$/Hydrocarbon Mole ratio | Avg Reactor Temp. ° F | LHSV Hr$^{-1}$ | Toluene Conv. Wt.% |
|---|---|---|---|---|---|---|
| 44 | 6 | 3,765 | 1.66 | 885 | 2.2 | 46.1 |
| 45 | 9 | 4,730 | 1.26 | 893 | 2.8 | 45.6 |
| 46 | 31 | 4,730 | 1.37 | 904 | 2.8 | 45.4 |
| 47 | 37 | 5,535 | 1.19 | 914 | 3.2 | 46.9 |
| 48 | 44 | 5,535 | 1.13 | 916 | 3.2 | 47.0 |
| 49 | 51 | 5,475 | 1.05 | 916 | 3.2 | 47.1 |
| 50 | 65 | 5,430 | 1.11 | 916 | 3.2 | 47.2 |
| 51 | 72 | 5,535 | 1.06 | 916 | 3.2 | 48.7 |
| 52 | 79 | 5,490 | 1.07 | 917 | 3.2 | 47.1 |
| 53 | 80 | 6,470 | 1.17 | 940 | 3.8 | 47.9 |
| 54 | 86 | 6,395 | 1.08 | 942 | 3.8 | 48.6 |
| 55 | 100 | 6,440 | 1.02 | 945 | 3.8 | 47.6 |
| 56 | 107 | 6,380 | 1.22 | 944 | 3.8 | 48.2 |
| 57 | 114 | 6,230 | 1.35 | 941 | 3.7 | 45.5 |
| 58 | 121 | 6,410 | 1.14 | 943 | 3.8 | 46.0 |
| 59 | 128 | 6,380 | 1.16 | 949 | 3.8 | 46.7 |
| 60 | 135 | 6,280 | 1.13 | 950 | 3.7 | 46.9 |
| 61 | 142 | 6,370 | 1.00 | 949 | 3.7 | 46.8 |
| 62 | 158 | 5,960 | 1.35 | 967 | 3.5 | 45.1 |

| Ex. | P-xylene MLBS/Hr | Xylenes MLBS/Hr | PX % (Xyl Basis) | PX Equil Conc. at T(*) | Approach to Equil |
|---|---|---|---|---|---|
| 44 | 2.422 | 9.734 | 24.88 | 23.27 | 107.0 |
| 45 | 3.192 | 12.768 | 25.00 | 23.25 | 107.5 |
| 46 | 3.065 | 12.319 | 24.88 | 23.24 | 107.0 |
| 47 | 3.605 | 14.556 | 24.76 | 23.22 | 106.6 |
| 48 | 3.975 | 15.563 | 25.54 | 23.22 | 110.0 |
| 49 | 4.129 | 16.250 | 25.40 | 23.22 | 109.4 |
| 50 | 3.998 | 15.658 | 25.53 | 23.22 | 109.9 |
| 51 | 4.113 | 16.186 | 25.41 | 23.22 | 109.4 |
| 52 | 3.748 | 14.383 | 26.05 | 23.22 | 112.2 |
| 53 | 4.811 | 18.916 | 25.43 | 23.18 | 109.7 |
| 54 | 4.816 | 18.490 | 26.05 | 23.18 | 112.4 |
| 55 | 4.870 | 18.167 | 26.81 | 23.16 | 115.8 |
| 56 | 5.068 | 18.504 | 27.39 | 23.16 | 118.3 |
| 57 | 5.035 | 18.080 | 27.85 | 23.18 | 120.1 |
| 58 | 5.014 | 17.664 | 28.39 | 23.16 | 122.6 |
| 59 | 4.970 | 17.432 | 28.51 | 23.15 | 123.2 |
| 60 | 4.973 | 17.292 | 28.75 | 23.14 | 124.2 |
| 61 | 5.458 | 17.972 | 30.36 | 23.15 | 131.1 |
| 62 | 4.684 | 15.114 | 31.00 | 23.13 | 134.0 |

*Para-xylene equilibrium concentration at the indicated average reactor temperature.

It will be noted from the examples of this invention that the vapor-phase disproportionation of toluene by contacting with the catalyst composition of this invention provides substantial benefits over disproportionation with other zeolite catalysts known in the art. For example, and possibly the most important fact, the catalyst composition for use herein exhibits markedly improved aging properties under the conditions of the present process, including economically attractive low hydrogen/hydrocarbon mole ratios. Instead of cycle periods of a few hours or days as has been the practice of the prior art, a cycle of weeks or months is possible, even at a hydrogen/ hydrocarbon mole ratio of zero.

In addition to being capable of giving high and selective product yields at low and even zero hydrogen/hydrocarbon mole ratio, the catalyst composition used in the process of this invention is easily and effectively regenerated, when necessary, utilizing adiabatic burning in the presence of an inert dry gas as an oxygen diluent. A suitable regeneration technique using an inert dry gas as an oxygen diluent may be according to the following example:

| Time | Reactor Inlet Temperature, °F | Mass Velocity, lb/hr-ft² Air |
|---|---|---|
| 0 | 650 | 11 |
| 1.5 | 675 | 11 |
| 4.0 | 800 | 11 |
| 22.0 | 850 | 11 |
| 25.0 | 900 | 11 |
| 25.5 | 950 | 11 |
| 26.5 | 1000 | 11 |
| 27.5 | 1000 | 1 |
| 28.0 | End of regeneration | |

Also, the catalyst composition employed in the process of this invention will withstand numerous regenerations without losing activity. Thus, it is contemplated that a catalyst life in commercial use may be several years.

Still further, the products of the present process comprise greater than equilibrium amounts of para-xylene.

It will be appreciated that the operating conditions for the reaction in accordance with the process of this invention, as exemplified in the foregoing examples, may be varied within the limits specified so that the process may be conducted in vapor-phase, and that various modifications and alterations may be made in the process without departing from the spirit and scope thereof.

What is claimed is:

1. A process for effecting vapor-phase disproportionation of toluene which comprises contacting toluene with a catalyst composition comprising a crystalline aluminosilicate zeolite characterized by a silica/alumina mole ratio of greater than 12 and a constraint index within the approximate range of 1 to 12 and containing cations which are predominately hydrogen, hydrogen precursor and/or a non-noble metal of Group VIII of the Periodic Table of Elements, said toluene having been dried prior to said contacting, under conditions effective for accomplishing said vapor-phase disproportionation including a reactor inlet temperature between about 650° F and about 1100° F, a hydrogen to hydrocarbon mole ratio of between 0 and about 4, a reactor pressure between atmospheric and about 1000 psig and a weight hourly space velocity of between about 1 and about 20, whereby from about 40 to about 50 weight percent of said toluene is disproportionated and the approach to equilibrium for para-xylene in the process is greater than 100%.

2. The process of claim 1 wherein said zeolite is ZSM-5.

3. The process of claim 1 wherein the reactor inlet temperature is between about 850° F and 1000° F and the reactor pressure is between about 400 and 800 psig.

4. The process of claim 1 wherein said catalyst composition comprises said crystalline aluminosilicate zeolite combined in an amount of between about 30 and about 90 weight percent in a binder therefor.

5. The process of claim 4 wherein said binder is alumina.

6. The process of claim 5 wherein said alumina binder is present in about 35 percent of the total catalyst composition.

7. The process of claim 1 wherein said cations are predominately hydrogen.

8. The process of claim 1 wherein said cations are predominately a non-noble metal of Group VIII of the Periodic Table.

9. The process of claim 8 wherein said cations are nickel.

10. The process of claim 1 wherein said hydrogen to hydrocarbon mole ratio is between 0 and about 3.

11. The process of claim 10 wherein said hydrogen to hydrocarbon mole ratio is between 0 and about 1.5.

12. The process of claim 11 wherein said hydrogen to hydrocarbon mole ratio is 0.

13. The process of claim 2 wherein the reactor inlet temperature is between about 850° F and 100° F and the reactor pressure is between about 400 and 800 psig.

14. The process of claim 2 wherein said catalyst composition comprises said crystalline aluminosilicate zeolite combined in an amount of between about 30 and about 90 weight percent in a binder therefor.

15. The process of claim 14 wherein said binder is alumina.

16. The process of claim 15 wherein said alumina binder is present in about 35 weight percent of the total catalyst composition.

17. The process of claim 2 wherein said cations are predominately hydrogen.

18. The process of claim 2 wherein said cations are predominately a non-noble metal of Group VIII of the Periodic Table.

19. The process of claim 18 wherein said cations are nickel.

20. The process of claim 2 wherein said hydrogen to hydrocarbon mole ratio is between 0 and about 3.

21. The process of claim 20 wherein said hydrogen to hydrocarbon mole ratio is between 0 and about 1.5.

22. The process of claim 21 wherein said hydrogen to hydrocarbon mole ratio is 0.

23. The process of claim 1 wherein said toluene has been dried by percolation through silica gel or a molecular sieve.

* * * * *

UNITED STATES PATENT AND TRADEMARK OFFICE
CERTIFICATE OF CORRECTION

PATENT NO. : 4,052,476
DATED : October 4, 1977
INVENTOR(S) : ROGER A. MORRISON

It is certified that error appears in the above-identified patent and that said Letters Patent are hereby corrected as shown below:

| | |
|---|---|
| Column 3, line 63 | "pyrrolidone" should read --pyrrolidine--. |
| Column 4, line 68 | "ratio" should read --ratios--. |
| Column 6, line 57 | "aluminosilicate" should read --aluminosilicates--. |
| Column 9, line 25 | "pyrrolidone" should read --pyrrolidine--. |
| Column 10, line 16 | "therof" should read --thereof--. |
| Column 10, line 52 | Insert the word --vessel-- between the words "reaction" and "employed". |
| Column 10, line 68 | "100 psig" should read --1000 psig--. |
| Column 12, line 3 | " 1 $NH_4NO_3$" should read --1 N $NH_4NO_3$--. |
| Column 13, line 22 | "appear" should read --appears--. |
| Column 20, line 27 | "15" should read --14--. |
| Column 20, line 33 | "means" should read --mass--. |
| Column 24, line 11 | Insert the word --weight-- between "35" and "percent". |

Signed and Sealed this

Twenty-fifth Day of April 1978

[SEAL]

Attest:

RUTH C. MASON
Attesting Officer

LUTRELLE F. PARKER
Acting Commissioner of Patents and Trademarks